(12) United States Patent
Schmelzeisen-Redeker et al.

(10) Patent No.: US 10,111,609 B2
(45) Date of Patent: Oct. 30, 2018

(54) METHOD FOR DETECTING A MALFUNCTION OF A SENSOR FOR MEASURING AN ANALYTE CONCENTRATION IN VIVO

(71) Applicant: ROCHE DIABETES CARE, INC., Indianapolis, IN (US)

(72) Inventors: Guenther Schmelzeisen-Redeker, Lorsch (DE); Arnulf Staib, Heppenheim (DE); Hans-Martin Kloetzer, Weinheim (DE)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 0 days.

(21) Appl. No.: 14/954,276

(22) Filed: Nov. 30, 2015

(65) Prior Publication Data
US 2016/0081596 A1    Mar. 24, 2016

Related U.S. Application Data

(63) Continuation of application No. 13/440,312, filed on Apr. 5, 2012, now abandoned, which is a continuation
(Continued)

(30) Foreign Application Priority Data

Oct. 5, 2009    (EP) .................................... 09012550

(51) Int. Cl.
*A61B 5/1495* (2006.01)
*A61B 5/1486* (2006.01)
(Continued)

(52) U.S. Cl.
CPC .......... *A61B 5/1495* (2013.01); *A61B 5/1468* (2013.01); *A61B 5/1486* (2013.01);
(Continued)

(58) Field of Classification Search
CPC ........................... A61B 5/7221; A61B 5/7203
See application file for complete search history.

(56) References Cited

U.S. PATENT DOCUMENTS 5,119,321 A    6/1992 Burton, Jr. et al.
5,768,124 A    6/1998 Stothers et al.
(Continued)

OTHER PUBLICATIONS

Medida, Srinivas. "IDC Engineering Pocket guide on industrial automation." (Aug. 9, 2007).*

*Primary Examiner* — Giovanni Astacio-Oquendo
*Assistant Examiner* — Adam Clarke
(74) *Attorney, Agent, or Firm* — Harness, Dickey & Pierce, P.L.C.

(57) ABSTRACT

The invention relates to a method for detecting a malfunction of a sensor for measuring an analyte concentration in vivo, wherein a series of measurement signals is produced by means of the sensor, and a value of a noise parameter is continually determined from the measuring signals, the noise parameter indicating how severely the measurement is impaired by interference signals. According to the invention, continually determined values of the noise parameter are used to determine how quickly the noise parameter changes, and the rate of change of the noise parameter is evaluated to detect a malfunction.

12 Claims, 3 Drawing Sheets

Related U.S. Application Data of application No. PCT/EP2010/005544, filed on Sep. 9, 2010.

(51) Int. Cl.
*A61B 5/145* (2006.01)
*A61B 5/1468* (2006.01)
*A61B 5/00* (2006.01)

(52) U.S. Cl.
CPC ........ *A61B 5/14532* (2013.01); *A61B 5/7203* (2013.01); *A61B 5/725* (2013.01); *A61B 5/746* (2013.01)

(56) References Cited

U.S. PATENT DOCUMENTS

| | | | |
|---|---|---|---|
| 5,859,392 A | 1/1999 | Petty | |
| 8,010,174 B2 | 8/2011 | Goode, Jr. et al. | |
| 8,120,355 B1 | 2/2012 | Stetson | |
| 2002/0138230 A1 | 9/2002 | Faymon et al. | |
| 2005/0215871 A1* | 9/2005 | Feldman | A61B 5/14514 600/309 |
| 2006/0052679 A1 | 3/2006 | Kotulla et al. | |
| 2009/0057148 A1 | 3/2009 | Wieder et al. | |
| 2009/0076361 A1 | 3/2009 | Kamath et al. | |
| 2009/0156924 A1 | 6/2009 | Shariati et al. | |
| 2009/0251164 A1 | 10/2009 | Haroun et al. | |
| 2010/0168538 A1 | 7/2010 | Keenan et al. | |
| 2011/0046887 A1* | 2/2011 | Veldhuis | G01N 33/74 702/19 |
| 2011/0184267 A1 | 7/2011 | Duke et al. | |
| 2011/0237917 A1* | 9/2011 | Roy | A61B 5/14532 600/365 |
| 2011/0313680 A1* | 12/2011 | Doyle, III | A61B 5/14532 702/19 |
| 2012/0078067 A1* | 3/2012 | Kovatchev | G06F 19/3437 600/301 |

* cited by examiner

METHOD FOR DETECTING A MALFUNCTION OF A SENSOR FOR MEASURING AN ANALYTE CONCENTRATION IN VIVO

CROSS-REFERENCE TO RELATED APPLICATIONS

This application is a continuation of U.S. patent application Ser. No. 13/440,312, filed Apr. 5, 2012, which is a continuation of International Patent Application No. PCT/EP2010/005544, filed Sep. 9, 2010, which claims the benefit and priority of European Patent Application No. 09012550.1, filed Oct. 5, 2009. The entire disclosures of the above applications are incorporated herein by reference.

BACKGROUND

The invention relates to a method for detecting a malfunction of a sensor for measuring an analyte concentration in vivo, wherein a series of measuring signals is produced by means of the sensor, and a value of a noise parameter is continually determined from the measuring signals, the noise parameter indicating how severely the measurement is impaired by interference signals.

A method of this type is described in U.S. Patent Application Publication No. 2009/0076361 A1, Kamuth et al., published Mar. 19, 2009. In the known method, a noise parameter is compared to a pre-determined threshold value. The value of the noise parameter exceeding the threshold value leads to the conclusion that there is a malfunction.

SUMMARY

The aim of monitoring sensors for in-vivo measurement of analyte concentrations is to detect possible malfunctions as early and reliably as possible. It is the object of the present invention to devise a way in which this goal can be attained even better.

Said object is met, for example, by a method for detecting a malfunction of a sensor for measuring an analyte concentration in vivo, wherein a series of measuring signals is produced by means of the sensor, and a value of a noise parameter is successively determined from the measuring signals, the noise parameter indicating how severely the measurement is impaired by interference signals, characterized in that values of the noise parameter that are being determined successively are used to determine how quickly the noise parameter changes and the rate of change of the noise parameter is analyzed in order to detect a malfunction.

In a method according to the invention, values of the noise parameter that are being determined successively are used to determine how quickly the noise parameter changes and the rate of change of the noise parameter is analyzed in order to detect a malfunction. A malfunction can be determined significantly more reliably by this means than by comparing the noise parameter to a defined pre-determined threshold value.

Implantable sensors can be used to measure analyte concentration in the human body in a continual or quasi-continual manner. Of particular interest in this context are analytes that change significantly over a time period of hours or days, such as is the case with glucose. Sensors for in-vivo measurement deliver a series of measuring signals, for example current or voltage values, which are correlated to the analyte concentration value to be determined by means of a functional correlation, and reflect said value after a calibration.

As with any measurement, the concentration-dependent measuring signals of in-vivo sensors are impaired by measuring errors. Aside from systematic measuring errors, which often lead to a consistent deviation, random measuring errors, which can be summarized by the term of noise, are of particular significance. In this context, noise is defined as both measuring errors originating from the sensor itself, e.g. electronic noise, and measuring errors that are based on an uncontrolled effect acting on the sensor, for example by means of movements, or transient deviation of the analyte concentration in the vicinity of the sensor from the analyte concentration at other sites in the body of the patient.

The extent to which a measurement is impaired by noise can be quantified by means of a noise parameter that can be calculated, for example, as standard deviation of an interference signal portion. For this reason, the first step in calculating the noise parameter usually is to determine which portion of a measuring value is based on interference signals. In the simplest case, it can be presumed as an approximation that a given measuring value is the sum of a useful signal that corresponds to the analyte concentration sought and an interference signal. For example, recursive filters, such as Kalman filters or polynomial filters, in particular Savitzky-Golay filters, can be used to separate the noise portion from the useful portion.

The noise portion is then obtained by calculating the difference between the measuring value and a value of the useful portion at time t that has been determined. The noise thus determined contains the less useful signal portions, the more precisely the useful portion was determined.

Once the noise portion has been obtained from a series of values, a noise-quantifying series of values of a noise parameters can be calculated. The noise parameter can be calculated, for example, as standard deviation of the noise signal values in a pre-determined interval. Variances, variation coefficients, interquartile regions or similar parameters, for example, can be used as noise parameters instead of the standard deviation.

The consecutive values of the noise parameter determined can be used to determine how quickly the noise parameter changes, and the rate of change of the noise parameter can be analyzed to detect a malfunction. A warning signal, for example, can be issued as a consequence of having detected a malfunction. A warning signal of this type can be used to alert a user to the existence of a malfunction. Alternatively or additionally, the warning signal can just as well cause the measuring system to no longer display measuring values or cause measuring values that have been determined to be marked as unreliable in a memory of the system.

Usually, rates of change are determined as the derivative of the changing parameter over time. A derivation over time is most easily determined numerically by calculating the difference between two consecutive values and dividing by the distance in time between the two values. However, said procedure is not well-suited for determining the rate of change of a noise parameter. This is due to the fact that the noise parameter itself is subject to strong noise such that relatively large differences may occur between two consecutive noise parameter values without this change being correlated to a significant change of the sensor or sensor surroundings. Therefore, the rate of change of the noise parameter is preferably determined using a smoothed series of noise parameter values.

Smoothing can be achieved, for example, by calculating the mean of a pre-determined number of consecutive noise parameter values. It is also feasible to perform smoothing of a series of noise parameter values using a recursive filter, for example a Kalman filter. A smoothed series of noise parameter values can be used to calculate a measure for the rate of change of the noise parameter, for example, by calculating the difference of consecutive values. Recursive filters, in particular Kalman filters, can also be used to perform smoothing of a series of values of the rate of change to allow these to be analyzed more easily.

The rate of change of the noise parameter can be analyzed by means of an evaluation function. A step function is a simple example of an evaluation function. A step function can be used to pre-define a threshold value to which the rate of change of the noise parameter is to be compared. Selecting the threshold value properly, one can conclude that a malfunction exists if the threshold value is exceeded. It is also feasible to use continual evaluation functions, which indicate, for example, the actual degree of reliability of measuring values. For this purpose, the evaluation function can be used for projection, in particular non-linear projection, to a pre-determined interval, for example from 0 to 1 or from 0 to 100.

According to an advantageous refinement of the invention, the threshold value is changed during sensor operation as a function of a measuring result. Said measuring result can be determined from measuring signals of the sensor, and, for example, indicate the analyte concentration or the value of the noise parameter. In this context, it is preferable to analyze at least one subsequent value of the rate of change or one subsequent value of the noise parameter in order to check if the exceeding of the threshold is significant.

In the case of an electrochemical sensor comprising a working electrode, a counter-electrode, and a reference electrode, it is advantageous for the measuring result, as a function of which the threshold value is changed, to be based on a measurement of the electrical potential of the counter-electrode. Measuring the electrical potential of the counter-electrode can be used to determine, for example, the electrical voltage between the working electrode and the counter-electrode or between the counter-electrode and the reference electrode. As described in U.S. Patent Application Publication 2009/0057148 A1, Weider et al., published Mar. 5, 2009, which is incorporated in this regard into the present application by reference, a measurement of the electrical potential of the counter-electrode can be used to detect a sensor malfunction. Therefore, also taking the potential of the counter-electrode into consideration in the analysis of a noise parameter, allows a malfunction to be detected more reliably and more rapidly. For example, the threshold value to which the rate of change of the noise parameter is compared, can be lowered as soon as a measurement of the electrical potential of the counter-electrode yields suspicious values that make a malfunction appear plausible, but do not yet allow a malfunction to be detected conclusively.

It is preferable to assign a malfunction determined by analysis of the rate of change to one of two or more classes. For example, a first warning signal can be generated as a consequence of an assignment to a first class, whereas a second warning signal is generated as a consequence of an assignment to a second class. A first warning signal can be used, for example, to indicate a less severe malfunction, which might possibly resolve itself, whereas the second warning signal can be used to signal a more severe malfunction. For example signal lights differing in color, for example yellow and red, and/or acoustical signals differing in intensity can be used for the first and second warning signal, respectively. The second warning signal can, for example, also effect a shut-down of a display of current measuring values of the analyte concentration.

In the simplest case, the assignment of a malfunction to one of multiple classes can be made by means of different threshold values. If the rate of change exceeds a first threshold value, the malfunction is assigned to the first class. If the rate of change is sufficiently large to also exceed the second threshold value, the malfunction is assigned to the second class.

The assignment of a malfunction to a second class can also depend on a further parameter to be compared to a further threshold value. The further parameter can, for example, be a time period during which the rate of change exceeds the threshold value. Accordingly, the assignment of a malfunction to the second class can be made to depend on how long the rate of change exceeds a pre-determined threshold value. The further parameter can, for example, just as well be the noise parameter itself or, in case an electrochemical sensor is used, it can be determined by a measurement of the potential of the counter-electrode.

The noise parameter used according to the invention can be a unit-less parameter and indicate the noise in relation to the intensity of a useful signal. Proceeding as mentioned, the noise parameter corresponds to the signal-to-noise ratio that is in use in many technical fields. However, in a method according to the invention, the noise parameter preferably characterizes the absolute intensity of the interference signals. This means that the interference signal portion is not standardized with respect to the useful signal in the calculation of the noise parameter. In this case, an increase in the useful signal, i.e. an increase of the analyte concentration, does not necessarily lead to the noise parameter being smaller, but may leave the noise parameter unchanged.

Another aspect of the present invention relates to a method for detecting a malfunction of a sensor for measuring an analyte concentration in vivo, wherein a series of measuring signals is produced by means of the sensor, a value of a noise parameter is successively determined from the measuring signals, the noise parameter indicating how severely the measurement signals are impaired by interference signals, and the noise parameter is compared to a threshold value that is changed during sensor operation as a function of a measuring result in order to detect a malfunction.

Said method can be combined with the preceding method described above by providing it to comprise features of the preceding method described above. In particular, the threshold value can be changed during sensor operation as a function of a measuring result. Said measuring result can be determined from measuring signals of the sensor, i.e. it can indicate, for example, the analyte concentration or the value of the noise parameter, or, in the case of an electrochemical sensor, it can be based on a measurement of the electrical potential of the counter-electrode.

Regardless of how a malfunction of an in-vivo sensor is determined in detail by analysis of a noise parameter, it is generally advantageous for the noise to be as low as possible. In order to reduce the noise, multiple measuring signals of the analyte concentration can be used to calculate one measuring value each, for example by calculating the mean, and multiple measuring values can be used to calculate one value of the noise parameter each. Measuring signals can be generated in quasi-continual manner by means of an in-vivo sensor. It is particularly advantageous, to generate more than five measuring signals per minute, for example more than 10 measuring signals. Calculation of the mean can be used to calculate from the measuring signals measuring values that are affected by noise to a much lesser degree than the measuring signals. In this context, the measuring signals can be calculated for consecutive time intervals by including all measuring signals that were measured in the respective time interval in the calculation of a measuring value. It is feasible to use sliding, i.e. overlapping, time intervals instead of consecutive time intervals.

DRAWINGS

Further details and advantages of the invention are illustrated based on one exemplary embodiment referring to the appended drawings. In the figures.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom.

Figure 1:
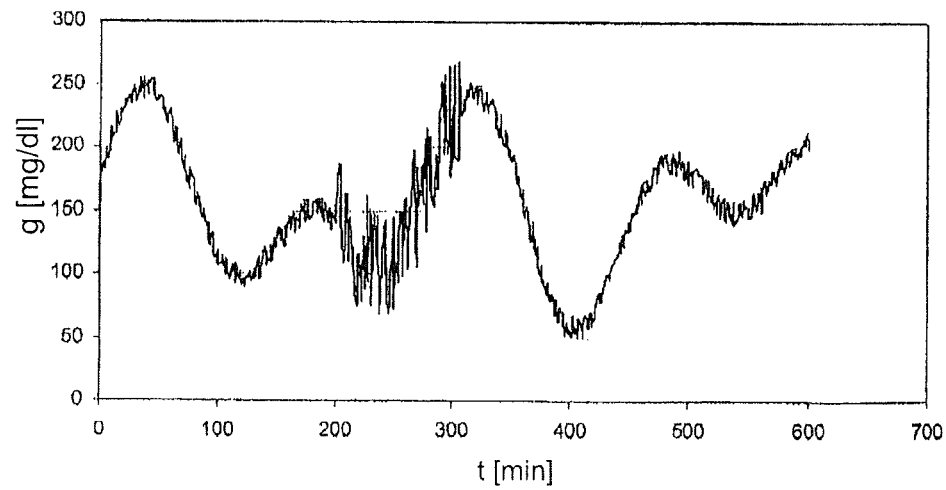
FIG. 1 shows an example of a series of measuring values of the glucose concentration.

FIG. 1 shows an example of a series of measuring values of the glucose concentration g as a function of the time t. The measuring values were generated by means of an electrochemical sensor under in-vivo conditions, whereby approximately 30 to 100 measuring signals were generated per minute from which one measuring value each was calculated as the arithmetic mean. The measuring values shown were each calculated for consecutive time intervals of one minute each.

Figure 2:
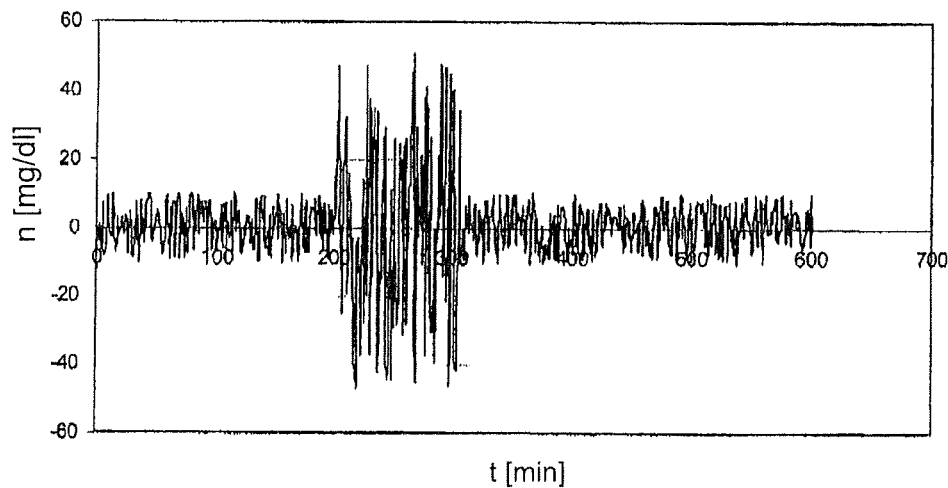
FIG. 2 shows the noise portion of the series shown in FIG. 1.

The course over time of the measuring values of the glucose concentration g shown in FIG. 1 is impaired by noise. The noise portion of the series of measuring values shown in FIG. 1 was determined by means of a recursive filter, for example a Kalman filter. The noise portion n is shown in FIG. 2 in units of mg/dl as a function of the time t in units of minutes. In this context, the noise portion ideally is the deviation of the measuring value of the glucose concentration from the actual and/or suspected glucose concentration g which was determined by analysis of the time course of the measuring values, for example by applying a Kalman filter.

Figure 3:
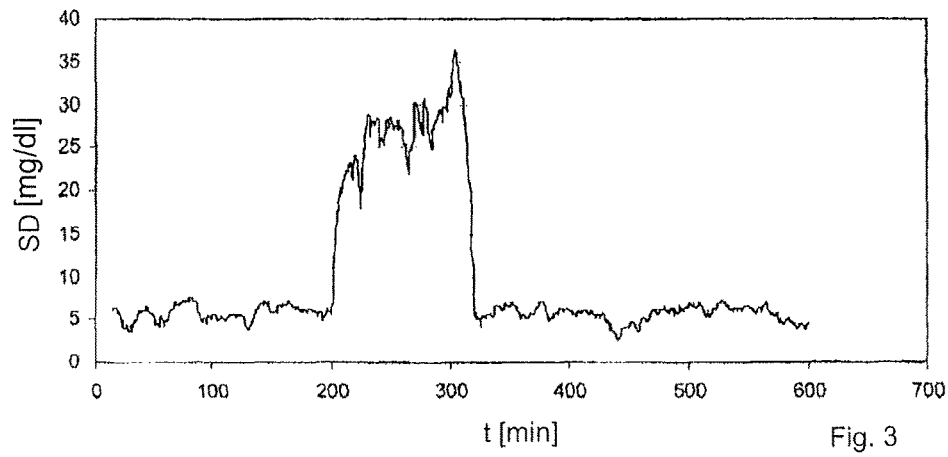
FIG. 3 shows the evolution of the noise parameter for the series shown in FIG. 1.

The noise portion n shown in FIG. 2 can be used to calculate a noise parameter that indicates how strongly the measurement is impaired by interference signals. In particular, the standard deviation of the noise portions determined for a time interval can be used as noise parameter. In FIG. 3, the standard deviation SD is plotted as a function of the time t, in units of minutes, as the noise parameter associated with the time course of the noise portion shown in FIG. 2, whose mean over time is zero. The standard deviation was calculated for sliding time windows of, for example, 15 minutes, in the example shown. In general, it is preferably to calculate the noise parameter for sliding time windows of at least 5 minutes, for example for time windows of 5 to 30 minutes, in particular 10 to 20 minutes.

Figure 4:
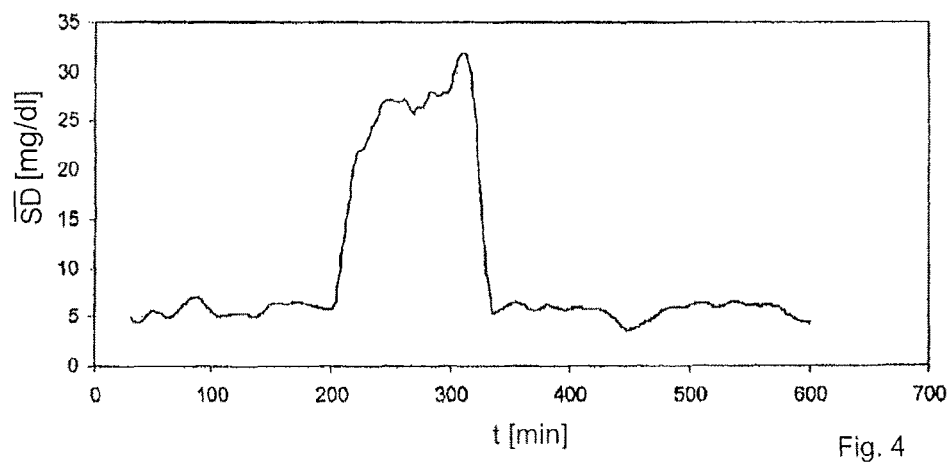
FIG. 4 shows the time course of the noise parameter after smoothing.

It is evident from FIG. 3 that the noise parameter SD itself is also impaired by noise. It can therefore be advantageous to smoothen the series of noise parameter values prior to further analysis of the noise parameter. This can be done, for example, by calculating the mean of the noise parameter values over a pre-determined time window. The time course of noise parameter values shown in FIG. 3 was smoothened by calculating the mean of all noise parameter values in a sliding time window of, for example, 15 minutes each. The result of said smoothing, i.e. the mean values $\overline{SD}$ that were calculated for the time windows, is shown in FIG. 4. Usually, it is advantageous to smoothen the noise parameter SD using sliding time windows of at least 5 minutes, for example using time windows of 5 to 30 minutes, in particular 10 to 20 minutes.

Figure 5:
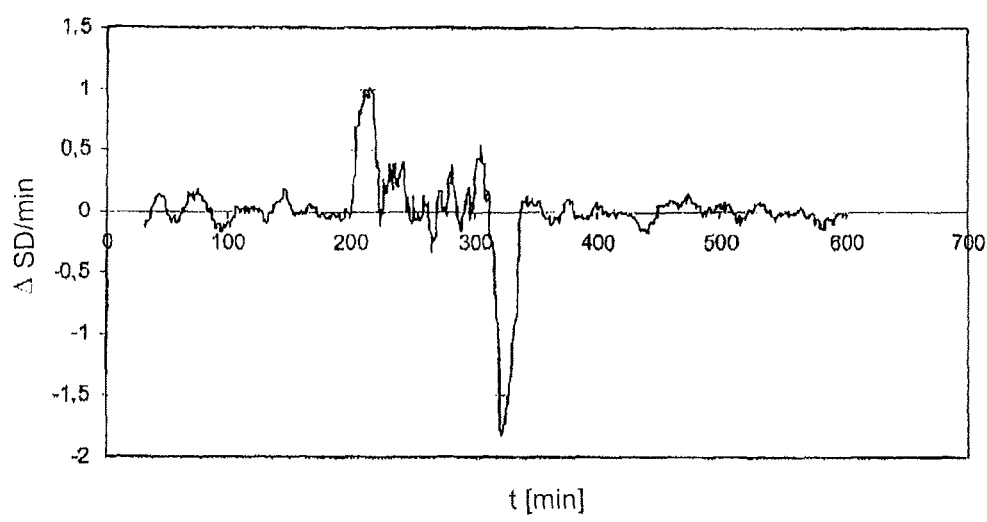
FIG. 5 shows the time course of the rate of change of the noise parameter.

The evolution of the noise parameter values SD and/or of the smoothened noise parameter values can be used to determine how rapidly the noise parameter changes. FIG. 5 shows the rate of change of the noise parameter SD determined by said means. The rate of change of the noise parameter can be determined, for example, as the derivative of the course shown in FIG. 4. The derivative with respect to time can be calculated numerically as the difference between consecutive values, whereby the difference is then divided by the time interval between the respective values. In a series of equidistant values, the rate of change is therefore proportional to the difference between consecutive values and is therefore denoted $\Delta SD$ in FIG. 5.

As is evident from FIG. 1 and in particular from FIG. 2 with the naked eye, the noise increased strongly between a time t of approximately 200 minutes and approximately 300 minutes. Said increased noise is particularly evident in FIGS. 3 and 4. The rate of change of the noise parameter shown in FIG. 5 is particularly well-suited for detecting precisely when the noise began to increase.

FIG. 5 evidences an increase in the rate of change $\Delta SD$ of the noise as a peak that is clearly distinct from the background. The end of the increased noise is indicated likewise by a peak pointing downwards. Accordingly, analysis of the rate of change $\Delta SD$ allows increased noise to be detected early and reliably and allows one to conclude that a malfunction is present. For this purpose, the rate of change of the noise can be compared, for example, to a pre-determined threshold value. The rate of change of the noise exceeding a pre-determined threshold value of, for example, half of a standard deviation of the noise per minute triggers the generation of a warning signal.

The analysis of the rate of change of the noise can be supplemented by analysis of the absolute intensity of the noise, for example a threshold for the noise parameter, or analysis of a measurement of the electrical potential of the counter-electrode, in particular for evaluation of the severity of the interference.

If the interference is rather minor, as is the case in the embodiment described above, a simple warning signal can be an appropriate response to malfunction of the sensor thus detected. If the malfunction is more severe as is characterized by more intense noise, for example an alarm signal can be generated and/or the measuring values of the glucose concentration g determined during the period of increased noise can be discarded as unreliable.

What is claimed is:

1. A method for detecting a malfunction of a sensor for measuring an analyte concentration in vivo, comprising:

producing a series of measuring signals, by means of the sensor;

determining successively a value of a noise parameter from the measuring signals, the noise parameter indicating how severely the measurement is impaired by interference signals;

determining the rate of change of the values of the noise parameter by calculating a time derivative of the noise parameter, wherein the rate of change of the noise parameter is determined on a smoothened series of values of the noise parameter; and analyzing the rate of change of the noise parameter in order to detect a malfunction, wherein in calculating the value of the noise parameter it is determined which portion of a measuring value is based on the interference signals such that a given measuring value is the sum of a useful signal that corresponds to the analyte concentration and the interference signal, and wherein a recursive filter is used to separate a noise portion from the useful portion of the measurement signal.

2. The method according to claim 1, wherein one value of a noise parameter each is determined for a pre-determined time interval.

3. The method according to claim 1, wherein the rate of change of the noise parameter is analyzed by comparing it to a threshold value.

4. The method according to claim 3, wherein the threshold value is changed during sensor operation as a function of a measuring result.

5. The method according to claim 4, wherein the sensor comprises a working electrode, a counter-electrode, and a reference electrode, whereby the measuring result is based on a measurement of the electrical potential of the counter-electrode.

6. The method according to claim 1, wherein a warning signal is generated as a consequence of the detection of a malfunction.

7. The method according to claim 1, wherein a malfunction that has been determined by the analysis of the rate of change is assigned to one of at least two classes.

8. The method according to claim 7, wherein the assignment is made as a function of the rate of change and of at least one further parameter.

9. The method according to claim 1, wherein the noise parameter characterizes the absolute intensity of the interference signals.

10. The method according to claim 1, wherein multiple measuring signals are used to calculate one measuring value each and multiple measuring values are used to calculate one value of the noise parameter each.

11. The method according to claim 10, wherein the measuring values are calculated by calculating the mean of multiple measuring signals.

12. The method according to claim 1, wherein the smoothened series of values of the noise parameter is obtained by calculating a mean of a pre-determined number of consecutive noise parameter values.

\* \* \* \* \*